United States Patent [19]

Lafontaine

[11] Patent Number: 5,662,621

[45] Date of Patent: Sep. 2, 1997

[54] GUIDE CATHETER WITH SHAPE MEMORY RETENTION

[75] Inventor: Daniel M. Lafontaine, Plymouth, Minn.

[73] Assignee: SciMed Life Systems, Inc., Maple Grove, Minn.

[21] Appl. No.: 498,887

[22] Filed: Jul. 6, 1995

[51] Int. Cl.[6] .................................................. A61M 25/00
[52] U.S. Cl. ........................................ 604/281; 604/95
[58] Field of Search ............................ 604/280–2, 98, 604/95; 600/143, 146; 264/230

[56] References Cited

U.S. PATENT DOCUMENTS

| | | | |
|---|---|---|---|
| 3,890,976 | 6/1975 | Bazell et al. | 128/351 |
| 4,776,844 | 10/1988 | Ueda | 604/95 |
| 4,909,787 | 3/1990 | Danforth | 604/282 |
| 4,944,727 | 7/1990 | McCoy | 604/95 |
| 4,969,709 | 11/1990 | Sogawa et al. | 350/96.26 |
| 4,969,890 | 11/1990 | Sugita et al. | 606/192 |
| 4,977,886 | 12/1990 | Takehama et al. | 128/4 |
| 4,994,047 | 2/1991 | Walker et al. | 604/264 |
| 5,025,799 | 6/1991 | Wilson | 604/281 |
| 5,055,101 | 10/1991 | McCoy | 604/201 |
| 5,114,402 | 5/1992 | McCoy | 604/95 |
| 5,222,949 | 6/1993 | Kaldany | 604/282 |
| 5,226,899 | 7/1993 | Lee et al. | 604/282 |
| 5,236,424 | 8/1993 | Imran | 604/280 |
| 5,254,088 | 10/1993 | Lundquist et al. | 604/95 |
| 5,267,982 | 12/1993 | Sylvanowicz | 604/281 |
| 5,330,466 | 7/1994 | Imran | 606/13 |
| 5,334,168 | 8/1994 | Hemmer | 604/281 |
| 5,334,171 | 8/1994 | Kaldany | 604/282 |
| 5,368,564 | 11/1994 | Savage | 604/95 |
| 5,381,782 | 1/1995 | DeLaRama et al. | 128/4 |
| 5,383,923 | 1/1995 | Webster, Jr. | 607/125 |
| 5,389,090 | 2/1995 | Fischell et al. | 604/280 |
| 5,443,454 | 8/1995 | Tanabe et al. | 604/264 |
| 5,482,029 | 1/1996 | Sekiguchi et al. | 604/281 |

Primary Examiner—Corrine M. McDermott
Assistant Examiner—Ellen Tao
Attorney, Agent, or Firm—Nawrocki, Rooney & Sivertson, P.A.

[57] ABSTRACT

Guide catheter incorporating a braided or braidless construction having increased performance characteristics for catheterization procedures. The guide catheter may include a shaft to provide support to the guide catheter for positioning the guide catheter within the patient's vascular system, and for providing a stimulus to the guide catheter for shaping the guide catheter. The guide catheter may be formed of memory retention material responsive to the stimulus for selectively shaping the guide catheter during a catheter procedure.

26 Claims, 3 Drawing Sheets

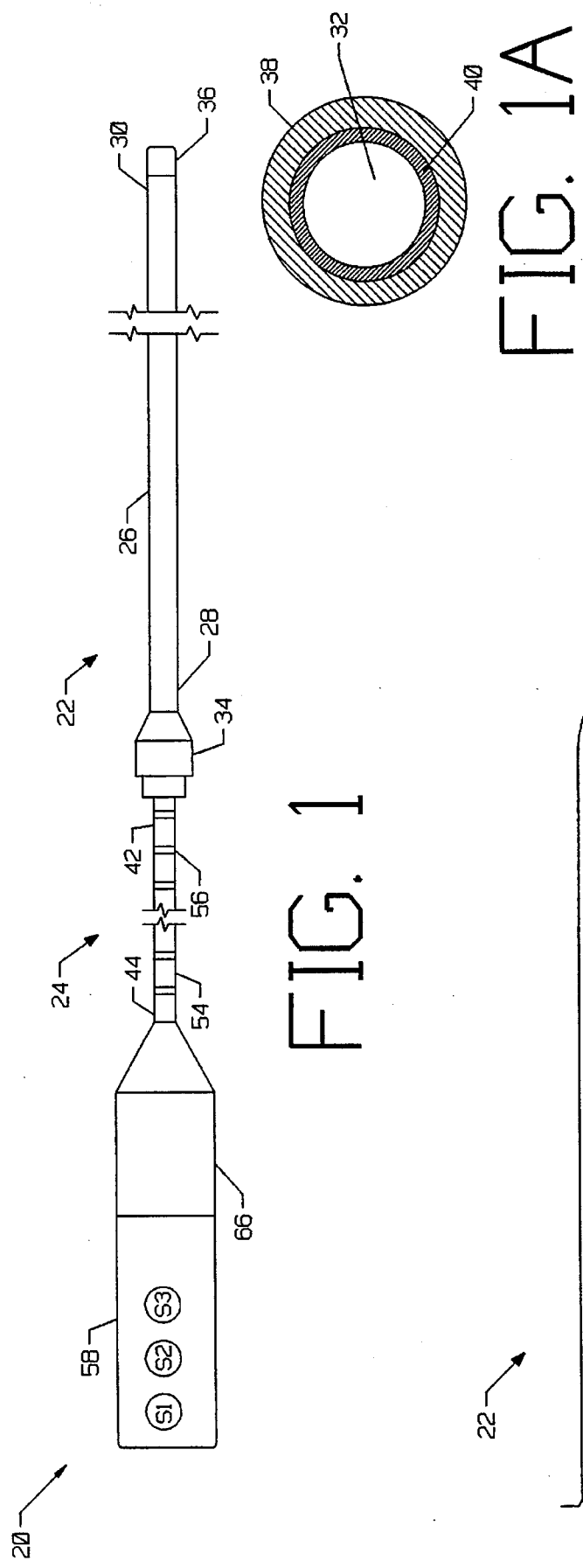
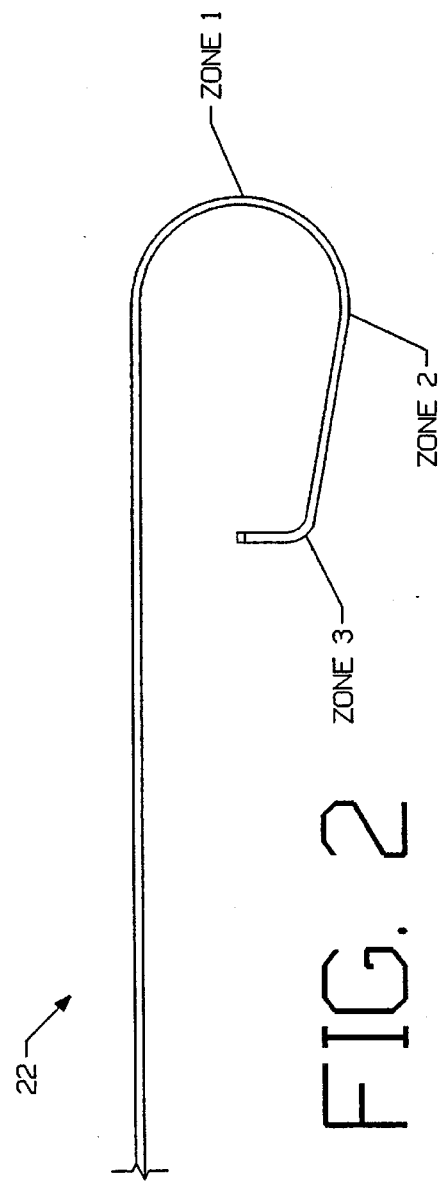

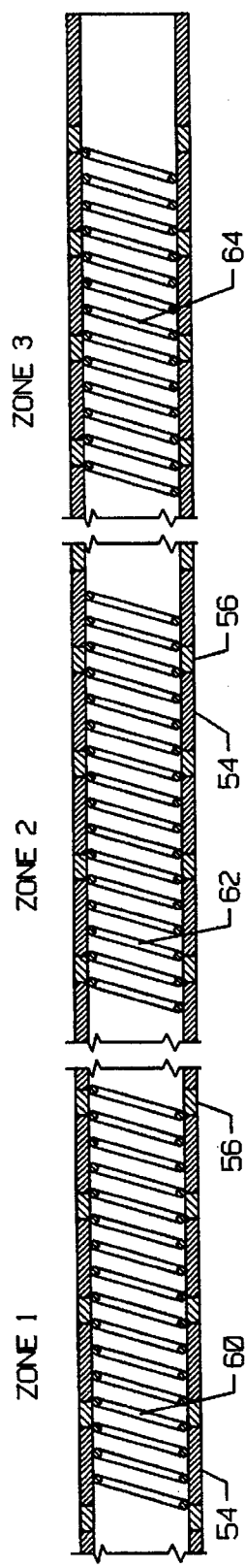
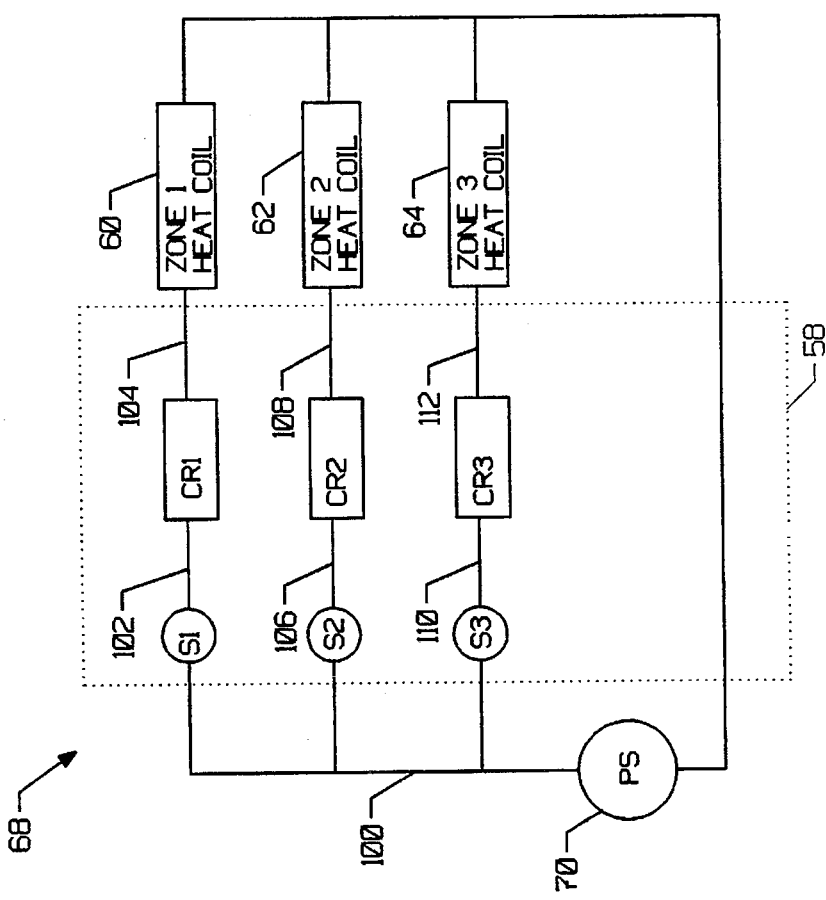
FIG. 3
FIG. 4

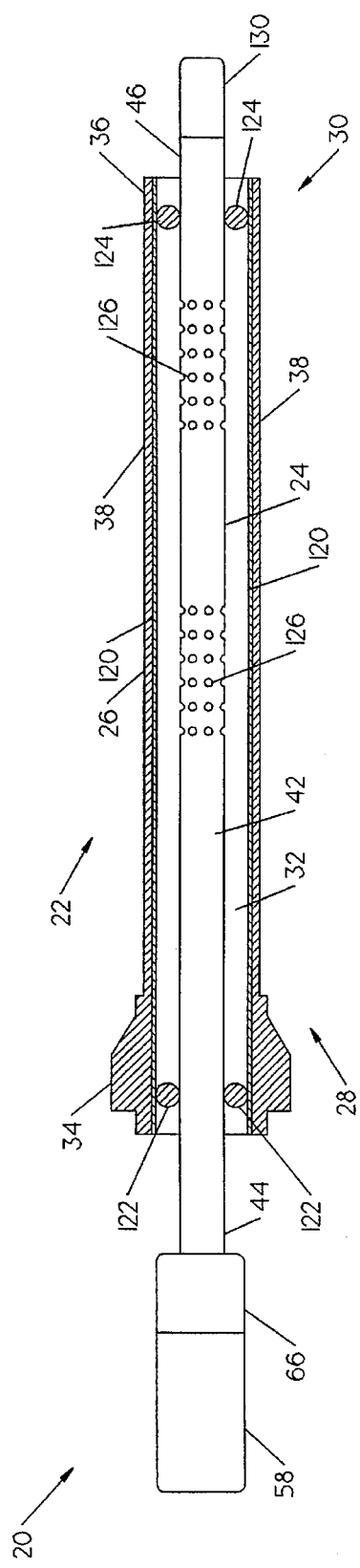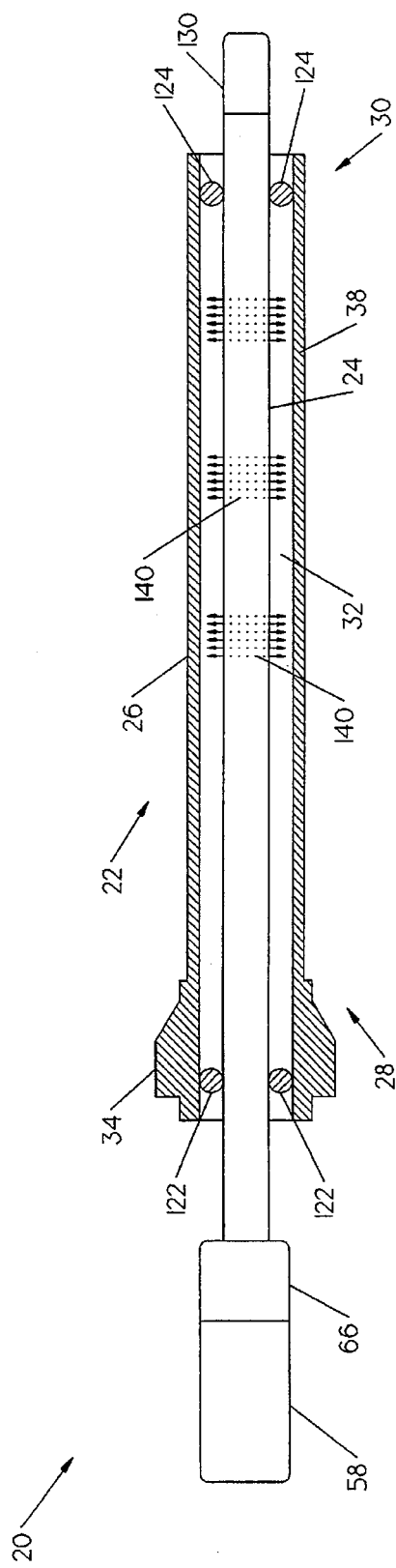

GUIDE CATHETER WITH SHAPE MEMORY RETENTION

FIELD OF THE INVENTION

The present invention relates to guide catheters and diagnostic catheters used in medical catheterization procedures. In particular, the present invention relates to an improved guide or diagnostic catheter having a simple catheter design, which is capable of being selectively curved or shaped to a desired form during catheter procedures.

DESCRIPTION OF THE PRIOR ART

Guide catheters and diagnostic catheters are well known for use in coronary catheterization and percutaneous transluminal coronary angioplasty (PTCA) procedures. Guide catheters aid in treatment of arterial lesions by providing a conduit for positioning dilatation balloon systems across an arterial stenosis. Guide catheters and diagnostic catheters work with various assemblies for performing other medical, therapeutic, and diagnostic procedures, such as dye delivery, arterial flushing, or arterial pressure monitoring.

Diagnostic catheters are used during cardiac catheterization for diagnosis of coronary artery disease in order to define vessel anatomy, isolate lesions, and identify adjacent cardiac branches which may impinge on the lesion and affect ventricular function.

For diagnosis of the coronary artery, the femoral artery is entered percutaneously and a sheath is inserted into the artery to provide access to the patient's vascular system. The diagnostic catheter is inserted into the femoral artery through this introducer sheath over a guide wire and advanced up the aorta to the aortic arch. Once over the aortic arch, the guide wire may be removed. A Y-adapter and manifold assembly are attached to the diagnostic catheter for implementation of diagnostic procedures, such as dye delivery, flushing capabilities, and arterial pressure monitoring.

The diagnostic catheter design generally includes a shaft having a proximal and a distal end. A lumen extends longitudinally through the shaft from the proximal to the distal end. Operably connected to the proximal end of the shaft is a hub assembly, for connection to catheterization equipment, and connected to the distal end of the shaft is a soft tip.

The distal end of the diagnostic catheter shaft is shaped to access the ostium of the coronary artery having the stenotic lesion. Different shapes may be employed for access to the ostium of a right or left coronary artery, mammary artery or the ostium of a bi-pass vein. During the diagnosis procedure, the physician advances and maneuvers the diagnostic catheter shaft within the artery, while at the same time injecting dye. The physician observes the dye using an angiography monitor for visualization of the patient's coronary system.

The diagnostic catheter is advanced and maneuvered until the distal end is properly engaged in the ostium of the coronary artery the physician believes to contain the stenosis. Once seated in the ostium, the physician injects additional dye for observations of obstruction to dye flow, indicative of the coronary disease.

For treatment of the coronary disease through angioplasty or other catheter based treatments, guide catheters are used. The guide catheters provide access to the area within the arterial system containing the stenotic lesion, and support for the treatment catheter which often includes a balloon dilatation system. Guide catheters are similar in construction to diagnostic catheters, although they are generally larger in size. Prior art guide catheters have a pre-shaped distal section or tip region to aid in access to the ostium of the coronary artery to receive treatment.

In operation, the guide catheter is introduced over a guide wire through a previously placed femoral introducer sheath and advanced up to the aortic arch. The guide wire can then be removed, and the guide catheter can be advanced and maneuvered until the guide catheter soft tip is properly engaged in the ostium of the coronary artery to be dilatated. A Y-adapter and manifold assembly are attached to the guide catheter hub at the proximal end for implementation of diagnostic procedures, such as dye delivery, flushing capabilities, pressure monitoring and delivery of the dilatation balloon system.

Diagnostic catheters and guide catheters are manufactured in hundreds of shapes and curve styles to accommodate anatomical variances in humans and to access specific areas within the coronary system. Curve shapes are also designed to provide support against the aortic wall when seated within the ostium, to resist the tendency for a catheter to "pop out" of the ostium (termed backout force) when injecting dye or advancing a treatment catheter into the artery. Catheters are presently specifically manufactured with high curve retention to maintain catheter placement within the ostium and to resist backout forces.

During angioplasty procedures, the catheters must be able to traverse tortuous pathways through blood vessels to the stenosis in a manner as atraumatic as possible. Therefore, to limit insertion time and discomfort to the patient, the catheter must be stiff enough to resist the formation of kinks, while at the same time the catheter must possess flexibility to be responsive to maneuvering forces when guiding the catheter through the vascular system. It is important that the guide catheter exhibit good torque control such that manipulation of a proximal portion of the guide catheter is responsively translated to the tip or distal end of the catheter to curve and guide the catheter through the tortuous pathways.

To meet the above performance requirements, guide catheters and diagnostic catheters are manufactured using polymers in conjunction with a braid of high-strength fibers or stainless steel wires incorporated into the tube. The guide catheters are generally formed of three layers: a first inner layer commonly formed of polytetrafluoroethylene to decrease the coefficient of friction between a therapeutic device and the guide catheter; a middle layer consisting of braided wire for torque control; and a third, outer layer commonly formed of polyethylene, polyurethane or a nylon-blend for stable positioning of the guide catheter, and providing backout support during other treatment procedures.

During diagnostic and therapeutic procedures, it is often necessary to use more than one shaped or curved catheter to access the right coronary, left coronary, mammary artery, or bypass vein for visualization of each vessel. The procedure of exchanging diagnostic catheters for visualization of different vessels requires more procedural time and exposes the patient to extended x-ray time and fluoroscopy. Additionally, hospitals are required to inventory hundreds of catheters with various curves, tip shapes and diameters to accommodate the various procedures for each patient.

It is desirable to be able to control the shape of a guide catheter during catheterization procedures. Additionally, it is desirable in catheter design for the inside diameter of the diagnostic or guide catheter to be maximized relative to the outside diameter, providing maximum space for dye flow and therapeutic device delivery. While designing catheters to meet these design goals, the catheters must continue to meet performance requirements of burst pressure requirements, kink resistance, curve retention, column strength, and torque control for advancement within the patient's vascular system.

SUMMARY OF THE INVENTION

The present invention relates to an improved guide or diagnostic catheter having a simple braided or braid-free catheter design, capable of changing shape during a catheter procedure, while performing the function of conventional diagnostic and guide catheters.

In a preferred embodiment, the present invention is a catheter assembly including a generally elongate shaft having a proximal end and a distal end. A lumen extends longitudinally between the proximal end and the distal end. Means are included for selectively providing a stimulus to at least a portion of the shaft. At least a portion of the shaft is formed of a material responsive to the stimulus for selectively changing the shape of at least a portion of the shaft.

In one preferred embodiment, the catheter shaft is changed between a generally ductile state and a relatively stiff state. The catheter may be curved in the stiff state. At least a portion of the shaft may be formed of a shape memory material.

In one preferred embodiment, the stimulus provided to at least a portion of the catheter shaft is thermal. The material responsive to the stimulus is a thermoset polymer. Alternatively, the stimulus may be a chemical or light.

The catheter assembly may further include means for changing position of a distal portion of the shaft while the catheter assembly is positioned within a patient's vascular system. Additionally, the means for providing a stimulus may further include at least one heating mechanism and means for selectively controlling the heating mechanism. In one embodiment, the heating mechanism is a resistance heat coil, and the means for selectively controlling the heating mechanism includes a power supply coupled to at least one switch.

In another embodiment, the present invention is a catheter assembly for changing the shape of a catheter during a catheter procedure. The catheter assembly includes a generally elongate shaft formed of shaped memory material having a proximal end and a distal end. A lumen extends longitudinally between the proximal end and the distal end. The catheter assembly includes a core member insertable within the lumen for selectively providing a stimulus to at least a portion of the catheter shaft. The portion of the shaft is formed of a material responsive to the stimulus for changing at least a portion of the shaft between a first ductile state and a second, relatively more stiff, curved state.

The material responsive to the stimulus may be a thermoset polymer. The core member may further comprise at least one heating member carried by the shaft and a control mechanism for selectively controlling the heating member. A mechanism may be included for selectively controlling a distal portion of the shaft while the shaft is in a ductile state.

The present invention further includes a method of positioning a tubular member within a patient's vascular system during a catheter procedure. The method includes providing an elongate shaft. The shaft is inserted within the patient's vascular system. An elongate tubular member formed of shaped memory material is advanced over the shaft, wherein the shaft provides a stimulus to at least a portion of the tubular member for changing the tubular member between a relatively stiff state and a softened, ductile state. The stimulus may be thermal, chemical, or light.

A distal end of the shaft is positioned within a ostium of the patient's vascular system. The method further comprises a step of controlling the stimulus provided by the shaft. The shaft is removed from the tubular member.

Yet another embodiment of the present invention includes a method of changing the shape of a tubular member located within a patient's vascular system. A core is provided having selectively controllable heating sections. The core is inserted within the tubular member. At least one heating section is heated for changing the shape of at least a portion of the tubular member formed of a thermoset polymer.

The present invention provides an economically feasible diagnostic or guide catheter design which may be shaped or curved as desired during a catheterization procedure. The catheter of the present invention is less costly to manufacture than conventional catheters, while meeting performance requirements for use, including reverse pressure requirements, kink-resistance, curve retention, column strength and torque control.

BRIEF DESCRIPTION OF THE DRAWINGS

The invention will be further described with reference to the accompanying drawings where like numbers refer to like parts in several views and wherein:

FIG. 1 is a perspective view showing the catheter assembly of the present invention including means for selectively stimulating disposed therein.

FIG. 1A is a cross-sectional view showing the catheter assembly of FIG. 1.

FIG. 2 is a perspective view showing the catheter of FIG. 1 in a curved state.

FIG. 3 is a partial cross-sectional view of the catheter core member shown in FIG. 1.

FIG. 4 is a simplified electrical block diagram of the catheter means for selectively stimulating of FIG. 1.

FIG. 5 is a longitudinal cross-sectional view of another embodiment of the catheter assembly of the present invention.

FIG. 6 is a longitudinal cross-sectional view of another embodiment of the catheter assembly of the present invention.

DETAILED DESCRIPTION OF THE PREFERRED EMBODIMENTS

The present invention relates to an improved guide or diagnostic catheter having a simple design, which is capable of performing the functions of conventional diagnostic and guide catheters. The present invention provides a diagnostic or guide catheter design which may be shaped or curved during a catheter procedure. The catheter of the present invention is less costly to manufacture than conventional catheters, while meeting performance requirements for use, including kink resistance, curve retention, column strength and torque control. Although references throughout this specification may be specifically made to either guide catheters or diagnostic catheters, references made to one are equally applicable to guide catheters, diagnostic catheters, and other therapeutic catheters.

The present invention provides a catheter (guide or diagnostic) which can be effectively positioned within the patient's coronary anatomy. The guide catheter of the present invention is formed from a memory retention material. The present invention includes a core which provides structural support to the guide catheter for steering the guide catheter through a patient's vascular system, while providing the memory retention stimulus to the guide catheter for shaping the guide catheter during a catheterization procedure. The guide catheter of the present invention may or may not include a braided middle layer.

FIG. 1 shows a perspective view of guide catheter assembly 20 in accordance with the present invention. FIG. 1A is a cross-sectional view of the catheter assembly 20 of FIG. 1. The catheter assembly 20 includes a guide catheter 22 positioned over a core 24. The core 24 provides the guide catheter 22 with the required performance torque response and kink resistance necessary for guiding the guide catheter 22 through the tortuous pathways of a patient's vascular system, while providing a memory retention stimulus to guide catheter 22.

The guide catheter 22 includes a shaft 26 having a proximal end 28 and a distal end 30. A lumen 32, shown in FIG. 1A, extends longitudinally through the shaft from the proximal end 28 to the distal end 30. Operably connected to the proximal end 28 of the shaft 26 is a hub assembly 34, and connected to the distal end 30 of the shaft 26 is a soft tip 36.

The guide catheter 22 shaft 26 is formed of a single extruded polymer layer 38 having memory retention characteristics, with a lubricous inner coating 40. The layer 38 provides for stable positioning within a patient's vascular system and backup support during catheter procedures. Preferably, the layer 38 is impregnated with a radiopaque material, such as barium sulfate or bismuth, to allow for partial visualization of the shaft 26 during catheter procedures.

The lubricous inner coating 40 allows for near frictionless movement of the core 24 within the guide catheter lumen 32. In a preferred embodiment, the lubricous inner coating is a hydrophilic coating. Alternatively, the guide catheter 22 may include an inner layer formed of a lubricous polymer, such as polytetrafluoroethylene.

In an alternative embodiment, it is recognized that the guide catheter 22 may be of a multilayered braided design as previously described herein. Guide catheter 22 may include a braided layer for additional response and support while positioning the guide catheter 22 within the patient's vascular system.

The guide catheter 22 is formed of a memory retention material. In a preferred embodiment, the guide catheter 22 is formed of a thermoset memory retention polymer, such as a thermoset polyethylene. Sections of the guide catheter 22 may be shaped and formed by heating and cooling of the guide catheter 22. Guide catheter 22 is pre-shaped with necessary curves to access the desired areas of the coronary anatomy.

Guide catheter 22 may be heated, softening guide catheter 22. In the heat softened state, guide catheter 22 is straight and easily deflectable. After guide catheter 22 is cooled, the memory retention properties of guide catheter 22 allows guide catheter 22 to return to its pre-shaped, relatively stiff, memory retention state.

Core 24 provides the stimulus to guide catheter 22 for transitioning guide catheter 22 between a soft, straight state and a pre-shaped, relatively stiff, memory retention state. Core 24 includes an elongate shaft 42 having a proximal end 44 and a distal end 46 (not shown). Core 24 is generally formed of alternating metallic sections 54 connected by elastomer joints 56. Preferably, the metallic sections 54 are formed of articulated stainless steel. Attached to the proximal end 44 of core 24 is control unit 58. Control unit 58 controls the stimulus provided by core 24.

In one preferred embodiment core 24 may be selectively heated in sections to provide the thermal stimulus to guide catheter 22. Referring to FIG. 2, guide catheter 22 is shown having sections which may be selectively heated labeled ZONE 1, ZONE 2, and ZONE 3. Referring to FIG. 3, core 24 includes heating coil 60, heating coil 62, and heating coil 64 which can be selectively controlled by control unit 58.

In one preferred embodiment, metallic sections 54 are cylindrical in shape and connected by elastomer joints 56. Located within the cylindrical core 24 are heating coils 60–64 which are formed of resistance wire.

In one preferred embodiment, heating coil 60 heats zone 1 of the guide catheter 22 shaft 26, which will form the aortic arch curve. Heating coil 62 heats zone 2 which will allow the distal tip of guide catheter 22 to be moved from side to side. Heating coil 3 heats zone 3 of guide catheter 22, which forms the curve of the distal tip 36. Each heating coil 60–64 may be selectively controlled at the control unit 58 by corresponding switches S1, S2, and S3. Switch S1 is electrically coupled to heating coil 60 to control zone 1, switch S2 is electrically coupled to heating coil 62 to control zone 2, and switch S3 is electrically coupled to heating coil 64 to control zone 3.

Additionally, deflection of the core 24 for shaping guide catheter 22 while it is in a soft state may be controlled at control unit 58 by mechanism 66. In the preferred embodiment, mechanism 66 is a pull wire mechanism which may selectively control deflection of core 24, by methods as disclosed in U.S. Pat. No. 5,383,923 to Webster which is herein incorporated by reference.

Additionally, it is also recognized that other mechanisms may be used for deflection of core 24 to change the shape of the guide catheter 22. For example, it is recognized that hydraulic cylinders, mechanical lead screws, and similar devices may be used to supply the mechanical stimulus to change the shape of the core 24 while the core 24 is positioned within the patient's vascular system. The forming core 24 may include an atraumatic spring coil tip to aid in navigating through the patient's vascular system. Additionally, core 24 or guide catheter 22 may include a separate lumen for delivery of contrast injection Y for visualization of placement of the guide catheter 22 distal end 36 within the ostium of the coronary artery receiving treatment.

Referring to FIG. 4, an electrical control diagram shown in schematic view showing selective control of each heating zone 1, zone 2, and zone 3 through control unit 58 switches S1, S2, and S3, is indicated generally at 68. In control diagram 68, power supply 70 is electrically coupled to switch 1, switch 2, and switch 3(100). Switch S1 is electrically coupled to current regulator CR1(102), and current regulator CR1 is electrically coupled to zone 1 heating coil 60(104). Switch S2 is electrically coupled to current regulator CR2(106), and current regulator CR2 is electrically coupled to zone 2 heating coil 62(108). Switch S3 is electrically coupled to current regulator CR3(110), and current regulator CR3 is electrically coupled to zone 3 heating coil 64(112). In a preferred embodiment, current regulators CR1, CR2, and CR3 are feedback controlled power amplifiers which provide constant regulated current to the corresponding heating coils 60, 62, and 64.

In operation, the core 24 is inserted within the guide catheter 22. The guide catheter 22 is formed of a shape-memory material, such as thermoset polymer, having pre-shaped curves located at zone 1, zone 2, and zone 3. Using control unit 58, switches S1, S2, and S3 are closed to activate heating coils 60, 62, and 64 into their heated state. When heated, heating coils 60, 62 and 64 heat the guide catheter 22 corresponding zones 1, 2, and 3. The thermoset polymer at the heated zones moves to a soft deflectable state, and guide catheter 22 takes on a generally straight shape.

The catheter assembly 20 is inserted through a previously placed sheath into the patient's vascular system and routed up over the aortic arch. The core 24 also provides support, steerability, and torquability to the guide catheter 22 for tracking the guide catheter 22 through the patient's vascular system and over the aortic arch.

Once positioned within the patient's vascular system, zones 1, 2, and 3, which are in a soft state, may be selectively deflected using a deflection mechanism 66. After achieving the desired guide catheter 22 position within the patient's coronary system, switches S1, S2, and S3 may be selectively opened, de-energizing heating coils 60, 62, and 64. The heating coils are cooled by the patient's vascular system. When cooling, the thermoset polymer construction of guide catheter 22 provides the guide catheter 22 pre-shaped zone 1, zone 2, and zone 3 to return to their relatively stiff, pre-shaped forms.

The guide catheter assembly may be further advanced and torqued to position the distal end 36 of the guide catheter 22 in the ostium of the coronary receiving treatment. The core 24 may now be removed to allow completion of the catheterization procedure. After treatment is completed, guide catheter 22 may be removed from the patient's vascular system in its generally rigid state. Alternatively, the core 24 may be again inserted into guide catheter 22 to heat guide catheter 22 for returning it to a ductile state for easy removal of guide catheter 22 from the patient's vascular system. The core 24 may be resterilized for reuse.

Core 24 may be re-inserted for softening guide catheter 22 to re-form guide catheter 22 for a new coronary position, such as switching the distal end 36 of guide catheter 22 from the left coronary artery to the right coronary artery. Additionally, contrast dies may be used to verify positioning of the guide catheter 22 within the patient's vascular system.

It is recognized that other heating and control methods may be used for core 24 while remaining within the scope of the present invention. Alternatively, heat may be provided to guide catheter 22 by other methods, such as resistance heat wires located within guide catheter 22 layer 38. Additionally, the heating coil may include a single zone, or may include a number of selectively controlled heating zones. The guide catheter 22 shaft 26 may be constructed of a number of thermoset polymers which allow at least portions of guide catheter 22 to move between a relatively soft state and a relatively more stiff pre-shaped state at desired temperatures.

Additionally, a series of pre-formed catheter shapes, as known in the art, may be imparted to the guide catheter 22, while guide catheter 22 is in a softened, ductile state within the patient's vascular system. The shapes may be imparted to the guide catheter 22 by use of memory retention nitinol wires in the core 24. The shapes imparted by the nitinol wires can be individually selected by electrical activation of shaped memory wires within the core 24.

It is recognized that other methods may be used for changing guide catheter 22 between a relatively soft, ductile state and a relatively stiff shape-memory state, such as softening by heat, light, or the use of chemicals. In each method, the shape and stiffness of guide catheter 22 may be changed while the guide catheter 22 is positioned within a patient's vascular system.

FIG. 5 shows yet another embodiment of the catheter assembly 20 in accordance with the present invention. In this embodiment, guide catheter 22 changes between a softened, ductile state and a relatively stiff state using chemical methods. Guide catheter 22 includes a thin inner lining 120, which is responsive to chemicals. Proximal seals 122 and distal seals 124 provide a liquid-tight seal between guide catheter 22 and core 24.

Core 24 includes openings 126 along shaft 42. Openings 126 are positioned between an internal lumen 128 of shaft 42 (not shown) and guide catheter 22 lumen 32. Additionally, core 24 may include a spring tip 130 to aid in positioning core 24 within a patient's vascular system.

In operation, core 24 provides a chemical stimulus to guide catheter 22 for changing guide catheter 22 between a relatively stiff state and a softened, ductile state. In one preferred embodiment, inner layer 120 is responsive to chemicals and formed of polycarbonate. A suitable solvent, such as methylinchloride (MEC) passes through control unit 58, through lumen 128, and openings 126 into lumen 32 in contact with catheter 22. Inner layer 120 is responsive to the chemical solvent and changes from a relatively stiff state to a softened, ductile state. Proximal seals 122 and distal seals 124 provide a liquid-tight seal such that the chemical solvent will not contact with bodily fluids. If contact with bodily fluids occurs, it is contemplated that the chemical solvent used may be safe for bodily contact, such as methylinchloride or alcohol.

Once guide catheter 22 is positioned within the patient's vascular system, the chemical solvent is flushed out of lumen 32, causing guide catheter 22 to return to a relatively stiff state.

Referring to FIG. 6, yet another embodiment of the present invention is shown where guide catheter 22 is changed between a relatively stiff state and a ductile state through exposure to ultraviolet (UV) rays or light. Control unit 58 connects core 24 to an ultraviolet or laser light source. Core 24 includes fibers 140 for communicating light between the light source and guide catheter 22. Fibers 140 may be selectively positioned along core 24 and selectively controlled by control unit 58. Guide catheter 22 is formed of a polymeric material which is responsive to ultraviolet or laser light for changing guide catheter 22 between a relatively stiff state and a ductile state.

In operation, guide catheter 22 is in a relatively stiff state. Using control unit 58, light fibers 140 are selectively energized, exposing guide catheter 22 to ultraviolet or laser light rays. The ultraviolet or laser light rays change guide catheter 22 from a relatively stiff state to a softened, ductile state. Guide catheter 22 is then positioned as desired within the patient's vascular system. Upon using control unit 58 to turn off the light source to guide catheter 22, guide catheter 22 returns to a relatively stiff state.

It will be understood, that this disclosure is, in many respects, only illustrative. Changes may be made in details, particularly in matters of shape, size,. material, and arrangement of parts without exceeding the scope of the invention. Accordingly, the scope of the invention is as defined within the language of the appended claims.

What is claimed is:

1. A catheter assembly comprising:
   a generally elongate shaft having a proximal end and a distal end, with a lumen extending longitudinally between the proximal end and the distal end;
   means for selectively providing a stimulus to at least a portion of the shaft including a core member insertable within the lumen; and
   wherein at least a portion of the shaft is formed of a material responsive to the stimulus for selectively changing at least a portion of the shaft between a generally softened, ductile state and a second, curved stiff state relative to the softened, ductile state.

2. The catheter assembly of claim 1, wherein at least a portion of the shaft is formed of a shape memory material.

3. The catheter assembly of claim 1, wherein the catheter includes at least one curve in the stiff state.

4. The catheter assembly of claim 1, wherein the stimulus is a thermal stimulus.

5. The catheter assembly of claim 1, wherein the stimulus is a chemical stimulus.

6. The catheter assembly of claim 1, wherein the stimulus is light.

7. The catheter assembly of claim 1, wherein the material responsive to the stimulus is a thermoset polymer.

8. The catheter assembly of claim 1, further including means for changing position of a distal portion of the shaft while the catheter assembly is positioned within a patient's vascular system.

9. The catheter assembly of claim 1, wherein the means for providing a stimulus further includes:

at least one heating mechanism; and means for selectively controlling the heating mechanism.

10. A catheter assembly comprising:

a generally elongate shaft having a proximal end and a distal end, with a lumen extending longitudinally between the proximal end and the distal end;

means for selectively providing a stimulus to at least a portion of the shaft;

wherein at least a portion of the shaft is formed of a material responsive to the stimulus for selectively changing at least a portion of the shaft between a generally softened, ductile state and a second curved stiff state relative to the softened, ductile state; and wherein the means for providing a stimulus further includes at least one heating mechanism and means for selectively controlling the heating mechanism, wherein the heating mechanism is a resistance heat coil.

11. The catheter assembly of claim 9, wherein the means for selectively controlling the heating mechanism includes a power supply coupled to at least one switch.

12. A catheter assembly for changing the shape of a catheter during a catheter procedure comprising:

a generally elongate shaft formed of shape memory material having a proximal end and a distal end, with a lumen extending longitudinally between the proximal end and the distal end;

a core member insertable within the lumen for selectively providing a stimulus to at least a portion of the catheter shaft; and wherein the portion of the shaft is formed of a material responsive to the stimulus for changing at least a portion of the shaft between a first ductile state and a second more stiff, curved state relative to said first state.

13. The catheter assembly of claim 12, wherein the material responsive to the stimulus is a thermoset polymer.

14. The catheter assembly of claim 12, wherein the core member further comprises:

at least one heating member carried by the shaft; and control mechanism for selectively controlling the heating member.

15. The catheter assembly of claim 12, further comprising a mechanism for selectively controlling a distal portion of the shaft while the shaft is in a ductile state.

16. A method of positioning a tubular member within a patient's vascular system during a catheter procedure, the method comprising:

providing an elongate shaft;

inserting the shaft within the patient's vascular system; and advancing an elongate tubular member formed of shape memory material over the shaft wherein the shaft provides a stimulus to at least a portion of the tubular member for changing the tubular member between a softened, ductile state and a second, curved, stiff state relative to the softened, ductile state.

17. The method of claim 16, wherein the stimulus is light.

18. The method of claim 16, further comprising the step of positioning a distal end of the shaft within an ostium of the patient's vascular system.

19. The method of claim 16, further comprising the step of controlling the stimulus provided by the shaft.

20. The method of claim 16, further comprising the step of removing the shaft.

21. The method of claim 16, wherein the stimulus is heat.

22. The method of claim 21, wherein at least a portion of the tubular member is selectively heated by a control mechanism coupled to a heat coil carried by the shaft.

23. The method of claim 16, wherein the stimulus is a chemical.

24. A method of changing the shape of a tubular member located within a patient's vascular system comprising the steps of:

providing a core having selectively controllable heating sections;

inserting the core within the tubular member; and heating at least one heating section for changing the shape of at least a portion of the tubular member formed of a thermoset memory retention polymer, wherein the portion of the tubular member is responsive to the heat provided by the heating section for changing the portion of the tubular member between a first, ductile state and a second, curved, more stiff state relative to said first, ductile state.

25. A catheter assembly for positioning and changing the shape of a catheter during a catheter procedure, the catheter assembly comprising:

a generally elongate shaft having a proximal end and a distal end, with a lumen extending longitudinally between the proximal end and the distal end, wherein the shaft includes a first section and a second section formed of a thermoset polymer;

a core member insertable within the lumen including first means for selectively providing a thermal stimulus to the shaft and second means for selectively providing a thermal stimulus to the shaft; and wherein the first section is responsive to the first means for providing a thermal stimulus, for changing the first section between a first ductile state and a second, curved more stiff state relative to said first state, and wherein the second section is responsive to the second means for providing a thermal stimulus for changing the second section between a first, ductile state and a second, curved, more stiff state relative to said first state.

26. The catheter assembly of claim 25, further comprising:

wherein the shaft further includes a third section formed of a thermoset polymer;

wherein the core member further includes third means for selectively providing a thermal stimulus to the shaft; and wherein the third section is responsive to the third means for selectively providing a thermal stimulus to the shaft for changing the third section between a first, ductile state and a second, curved, more stiff state relative to said first state.

* * * * *